United States Patent [19]

Bolich, Jr. et al.

[11] Patent Number: 4,472,375
[45] Date of Patent: * Sep. 18, 1984

[54] HAIR CONDITIONING COMPOSITIONS

[75] Inventors: Raymond E. Bolich, Jr., Maineville; Lloyd B. Hartsough; Philip E. Cothran, both of Cincinnati, all of Ohio

[73] Assignee: The Procter & Gamble Company, Cincinnati, Ohio

[*] Notice: The portion of the term of this patent subsequent to Feb. 22, 2000 has been disclaimed.

[21] Appl. No.: 432,199

[22] Filed: Oct. 1, 1982

Related U.S. Application Data

[63] Continuation of Ser. No. 234,297, Feb. 17, 1981, Pat. No. 4,374,825, which is a continuation-in-part of Ser. No. 218,376, Dec. 28, 1980, abandoned, which is a continuation-in-part of Ser. No. 128,436, Mar. 10, 1980, abandoned.

[51] Int. Cl.$^3$ .............................................. A61K 7/06
[52] U.S. Cl. ...................................................... 424/70
[58] Field of Search ........................................ 424/70

[56] References Cited

U.S. PATENT DOCUMENTS

| | | |
|---|---|---|
| 128,436 | 3/1880 | Bolich et al. |
| 2,826,551 | 3/1958 | Geen ................................... 252/121 |
| 3,439,088 | 4/1969 | Edman ................................ 424/358 |
| 3,577,528 | 5/1971 | McDonough et al. ............... 424/70 |
| 3,818,105 | 6/1974 | Coopersmith et al. .............. 424/358 |
| 3,932,610 | 1/1976 | Rudy et al. ........................... 424/70 |
| 4,206,196 | 6/1980 | Davis ................................... 424/70 |
| 4,374,825 | 2/1983 | Bolich, Jr. et al. ................... 424/70 |

FOREIGN PATENT DOCUMENTS

| | | |
|---|---|---|
| 666421 | 4/1967 | South Africa . |
| 676094 | 3/1968 | South Africa . |
| 849433 | 9/1960 | United Kingdom . |
| 2025228 | 1/1980 | United Kingdom . |

OTHER PUBLICATIONS

Todd, C. W. and Hayes, S., "Silicones Provide Real Benefits for Aerosol Cosmetics,", *American Perfumer and Cosmetics, 86(10), pp. 112–115 (1971).*
"Siloxane SWS-03314," SWS Silicones Corporation, Feb. 1975.
"Volatile Silicone 7158", *Cosmetic Formulary,* 1976.
Todd, C. and Byers, T., "Volatile Silicone Fluids for Cosmetic Formulations," *Cosmetics and Toiletries,* 96(1), pp. 29–32 (1976).
"Volatile Silicone 7207," *Cosmetic Formulary,* 1976.
Exxon Chemicals Technical Service Formula Sheet, "Balsam Creme Rinse HF948A01".
*Chemical Abstracts,* Vol. 80, No. 8, Feb. 25, 1974, p. 261, col. 2, No. 40939W.

*Primary Examiner*—Delbert R. Phillips
*Assistant Examiner*—F. T. Moezie
*Attorney, Agent, or Firm*—Richard C. Witte; John V. Gorman; Douglas C. Mohl

[57] ABSTRACT

Hair conditioning compositions in the form of an emulsion comprising a volatile agent, a nonionic, water soluble thickening agent, a cationic hair conditioning agent and water.

1 Claim, No Drawings

HAIR CONDITIONING COMPOSITIONS

CROSS REFERENCE TO RELATED APPLICATION

This is a continuation of our copending application Ser. No. 234,297 filed Feb. 17, 1981, now U.S. Pat. No. 4,374,825, which is a continuation-in-part of our application Ser. No. 218,376, filed Dec. 28, 1980 which was a continuation-in-part of our application Ser. No. 128,436, filed Mar. 10, 1980, the latter two now abandoned.

TECHNICAL FIELD

The present invention is related to hair conditioning compositions which can condition hair while not leaving an undesirable residue.

Some hair is naturally difficult to manage and to comb in the wet state, while other types of hair have become so as a result of the various treatments to which the hair has been subjected, such treatments including permanent waving, dyeing, tinting, frequent teasing, exposure to various atmospheric conditions, etc. Hair that has been subjected to an oxidizing condition, e.g. treatments with hydrogen peroxide or atmospheric oxygen photocatalyzed by sunlight, is especially difficult to comb in the wet state.

Many products are marketed for use at home and in the beauty shops to obviate and overcome the difficulty encountered in wet-combing. However, these products usually affect the hair's ability to maintain a set and stay clean.

Some of the cream rinse products which provide good wet-combing of the hair contain quaternary ammonium compounds. Their use produces a dilemma, their effectiveness as a wet-combing aid is proportional to the amount of cream rinse retained on the hair but the rate at which the hair appears and feels dirty is also proportional to that amount.

BACKGROUND ART

The use of volatile actives in hair care products is known. U.S. Pat. No. 3,577,528, May 4, 1971 to McDonough discloses two phase hair conditioners comprising an aqueous phase which contains a quaternary compound and a hydrocarbon or fluorinated hydrocarbon water immiscible phase. Rudy et al in U.S. Pat. No. 3,932,610, Jan. 13, 1976 discloses a shampoo composition which may contain a volatile hydrocarbon solvent. U.S. Pat. No. 3,818,105, June 18, 1974 to Coopersmith et al discloses hair conditioners containing a $C_{12}$ to $C_{14}$ isoparaffinic hydrocarbon fraction. South African patent application No. 666421, Apr. 12, 1967, Dasher and Fainer, discloses hair conditoners containing volatile silicones.

While these references disclose compositions which contain components of the type present in the compositions of the present invention they are not entirely satisfactory, either lacking in stability or performance.

It is therefore an object of the present invention to provide hair conditioners which overcome problems associated with prior compositions.

It is a further object of the present invention to provide an improved method of conditioning hair.

These and other objectives will become more apparent from the disclosure which follows.

DISCLOSURE OF THE INVENTION

The present invention relates to hair conditioning compositions in the form of emulsions comprising from about 1% to about 13% of a volatile liquid hydrocarbon or silicone hair conditioning agent, from about 0.1% to about 8% of a substantially nonionic, water soluble thickening agent, from about 0.05% to about 4% of a cationic hair conditioning agent and water.

DETAILED DESCRIPTION OF THE INVENTION

The compositions of the present invention comprise the above described essential components and may additionally contain several optional components. Each of the components is discussed in detail below.

Volatile Agent

The hydrocarbon and silicone agents useful in the present compositions have a boiling point in the range of about 99° C. to about 260° C. and have a solubility in water of less than about 0.1%. The hydrocarbons may be either straight or branched chain and may contain from about 10 to about 16, preferably from about 12 to about 16 carbon atoms. Examples of suitable hydrocarbons are decane, dodecane, tetradecane, tridecane and mixtures thereof.

The volatile silicones useful in the compositions of the present invention may be either a cyclic or a linear polydimethylsiloxane. The number of silicon atoms in the cyclic silicones is preferably from about 3 to about 7, more preferably 4 or 5.

The general formula for such silicones is

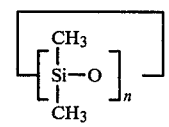

wherein n=3–7

The linear polydimethylsiloxanes have from about 3 to 9 silicon atoms and have the general formula $(CH_3)_3Si-O-Si(CH_3)_2-O-_n-Si(CH_3)_3$ n=1–7 Silicones of the above type, both cyclic and linear, are offered by Dow Corning Corporation, Dow Corning 344, 345 and 200 fluids, Union Carbide, Silicone 7202 and Silicone 7158, and Stauffer Chemical, SWS-03314.

The linear volatile silicones generally have viscosities of less than about 5 centistokes at 25° C. while the cyclic materials have viscosities less than about 10 centistokes. "Volatile" means that the material has a measurable vapor pressure. A description of volatile silicones is found in Todd and Byers, "Volatile Silicone Fluids for Cosmetics", *Cosmetics and Toiletries*, Vol. 91, January, 1976, pp 27–32, incorporated herein by reference.

The volatile agent is present in the compositions of this invention at a level of from about 1% to about 13%, preferably from about 2% to about 10%. The volatile silicones are the preferred volatile agents.

Nonionic Thickening Agent

The water soluble thickening agent useful in the present compositions is a substantially nonionic water soluble polymer. The polymers are those which exhibit viscosities exceeding about 200 poises at low shear, about $10^{-2}$ sec$^{-1}$, when their viscosities at 500 sec$^{-1}$ are less than about 9 poises. Preferred are those polymers which show about a 100 fold increase in viscosity over the shear rate range of 500 to $10^{-2} \sec^{-1}$. Included among such polymers are polyoxyethylene, guar gum, methylcellulose, methyl hydroxypropyl cellulose, polypropyl hydroxyethyl cellulose, locust bean gum, hydroxypropyl guar gum, hydroxypropyl cellulose, starches and starch derivatives such as hydroxyethyl amylose and starch amylose and mixtures thereof. Preferred polymers are guar gum and hydroxypropyl guar gum.

The water soluble thickening agent is present in the present compositions at a level of from about 0.1% to about 8%, preferably from about 0.5% to about 6.0%.

Cationic Hair Conditioning Agent

The cationic hair conditioning agent of the present compositions may be either a quaternary ammonium salt or the salt of a fatty amine.

Quaternary ammonium salts have the formula:

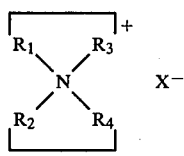

Wherein $R_1$ is hydrogen, an aliphatic group of from 1 to 22 carbon atoms, or aromatic, aryl or alkaryl groups having from 12 to 22 carbon atoms; $R_2$ is an aliphatic group having 1–22 carbon atoms; $R_3$ and $R_4$ are each alkyl groups of from 1 to 3 carbon atoms, and X is an anion selected from halogen, acetate, phosphate, nitrate and methyl sulfate radicals. The aliphatic groups may contain, in addition to carbon and hydrogen atoms, ether linkages as well as amido groups among other groups.

Preferred quaternary ammonium salts are the dialkyl dimethyl ammonium chlorides, wherein the alkyl groups have from 12 to 22 carbon atoms and are derived from long-chain fatty acids, such as hydrogenated tallow. The term "tallow" refers to fatty alkyl groups derived from tallow fatty acids. Such fatty acids give rise to quaternary compounds wherein $R_1$ and $R_2$ have predominately from 16 to 18 carbon atoms. The term "coconut" refers to fatty acid groups from coconut oil fatty acids. The coconut-alkyl $R_1$ and $R_2$ groups have from about 8 to about 18 carbon atoms and predominate in $C_{12}$ to $C_{14}$ alkyl groups.

Representative examples of quaternary ammonium salts of the invention include ditallow dimethyl ammonium chloride; ditallow dimethyl ammonium methyl sulfate; dihexadecyl dimethyl ammonium chloride; di(hydrogenated tallow) dimethyl ammonium chloride; dioctadecyl dimethyl ammonium chloride; dieicosyl dimethyl ammonium chloride; didocosyl dimethyl ammonium chloride; di(hydrogenated tallow) dimethyl ammonium acetate; dihexadecyl diethyl ammonium chloride; dihexadecyl dimethyl ammonium acetate; ditallow dipropyl ammonium phosphate; ditallow dimethyl ammonium nitrate; di(coconutalkyl)dimethyl ammonium chloride; and stearyl dimethyl benzyl ammonium chloride;

Other quaternary ammonium salts useful herein are the compounds of the formula

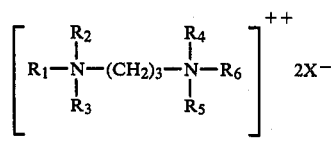

wherein $R_1$ is an aliphatic group having 16 to 22 carbon atoms, $R_2$, $R_3$, $R_4$, $R_5$ and $R_6$ are the same or different and are selected from H and alkyls having 1–4 carbon atoms and X is an anion as above defined. Tallow propanediammonium dichloride is an example of this quaternary ammonium salt.

Quaternary imidazolinium salts have the formula

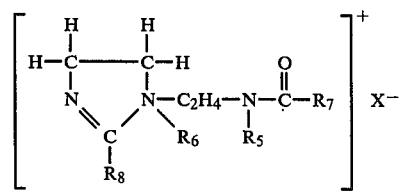

wherein $R_6$ is an alkyl group containing from 1 to 4, preferably from 1 to 2 carbon atoms, $R_5$ is an alkyl group containing from 1 to 4 carbon atoms or a hydrogen radical, $R_8$ is an alkyl group containing from 1 to 22, preferably at least 15 carbon atoms or a hydrogen radical, $R_7$ is an alkyl group containing from 8 to 22, preferably at least 15 carbon atoms, and X is an anion, preferably chloride.

Other suitable anions include those disclosed with reference to the quaternary ammonium salts described hereinbefore.

Particularly preferred are those imidazolinium salts in which both $R_7$ and $R_8$ are alkyls of from 12 to 22 carbon atoms, e.g., 1-methyl-1-[(stearoylamide)ethyl)]-2-heptadecyl-4,5-dihydroimidazolinium chloride; 1-methyl-1-[(palmitoylamide)ethyl]-2-octadecyl-4,5-dihydroimidazolinium chloride and 1-methyl-1-[(tallowamide)-ethyl]-2-tallow-imidazolinium methyl sulfate.

Included as a suitable hair conditioner herein are salts of fatty amines. As used herein the amines may be primary, secondary or tertiary but the alkyl, substituted and unsubstituted groups preferably have from 12-22 carbon atoms. Preferred are the primary and secondary amines with the primary being the most preferred. Diamines having a long chain alkyl group may also be used. Examples of amines suitable for use include dimethyl stearamine, dimethyl soyamine, stearylamine, soyamine, myristylamine, tridecylamine, ethyl stearylamine, N-tallow propanediamine, ethoxylated (5 moles E.O.) stearylamine dihydroxyethyl stearylamine and arachidylbehenylamine. The anions of the salts include those mentioned previously for the quaternary ammonium salts. Specific amine salts include stearylamine hydrochloride, soyamine chloride, stearylamine formate and N-tallow propanediamine dichloride.

The cationic hair conditioning agent is present at a level of from about 0.05% to about 4%, preferably from about 0.1% to about 2%, in the compositions of the instant invention. cl Water Water, preferably, distilled water is the final essential component of the present compositions. Water makes up the remainder of the compositions and is generally present at a level of up to about 95%, preferably from about 75% to about 90%.

Optional Components

In addition to the above described essential components the present compositions may contain a wide variety of optional components. The optional components can be materials which are soluble in the volatile agent phase, in the aqueous phase or not soluble in either phase.

Included among materials soluble in the volatile agent phase are hydrophobic polymers such as polyvinyl isobutyl ether, waxes such as cetyl alcohol and paraffin, and oils such as mineral oil, isopropyl myristate and non-volatile silicones. Agents which are soluble in the aqueous phase include acrylamide and polyoxyethylene resins.

Among other optional components are dyes, perfumes, opacifiers, pearlescent aids, buffers, preservatives, antioxidants, and antidandruff aids such as zinc pyrithione and sulfur.

Method of Manufacture

There are many approaches for making the hair conditioning compositions of the present invention. The approach selected should provide particles of the volatile agent in the range of from about 1 to about 10 microns. This can be accomplished by adding the volatile agent phase to the aqueous phase or vice versa. Suitable processes are shown in the Examples.

Industrial Applicability

The hair conditioning compositions of the present invention are preferably used as a rinse on freshly shampooed hair. The compositions are used in an amount of from about 1 g. to about 60 g., preferably from about 5 g. to about 30 g. and is then rinsed from the hair.

The following examples further describe and demonstrate embodiments within the scope of the present invention. The examples are given solely for the purpose of illustration and are not to be construed as limitations of the present invention as many variations thereof are possible without departing from its spirit and scope.

Unless otherwise indicated, all percentages herein are by weight.

EXAMPLE I

The following composition was prepared:

| | |
|---|---|
| Dow Corning Fluid 344[1] (cyclic silicone having 4 dimethyl siloxane groups) | 6.00% |
| Jaguar HP-60[2] (hydroxypropyl guar gum) | 1.00 |
| Adogen 432[3] (dicetyl dimethyl ammonium chloride) | 0.40 |
| Formaldehyde | 0.02 |
| Distilled Water q.s. | 100.00% |

[1]Supplied by Dow Corning Corporation.
[2]Supplied by Stein-Hall & Co., Inc.
[3]Supplied by Sherex Chemical Company The above composition was prepared by dispersing 10 grams of Jaguar HP-60 in 926 grams of distilled water using Lightnin ® Mixer. The mixture was heated to about 65° C. to fully dissolve and hydrate the Jaguar gum. Four grams of Adogen 432 were then added and dispersed. The silicone fluid was added next and dispersed. A high shear mixer, an Ultra Turrax ® Model 45S4 dispersator supplied by Tekmer Company, was finally used to further reduce the silicone particle size to about 1 to about 10 microns. The formaldehyde was added as the batch cooled to room temperature.

EXAMPLE II

The following composition of the present invention is prepared in a manner similar to that described in Example I.

| | |
|---|---|
| Union Carbide 7158 Silicone Fluid[1] (Cyclic silicone fluid having 5 dimethyl siloxane groups) | 8.00% |
| Supercol U[2] (guar gum) | 0.90 |
| Ditallow dimethyl ammonium chloride[3] | 1.00 |
| Perfume | 0.50 |
| Ethanol | 8.00 |
| Distilled water q.s. | 100.00% |

[1]Supplied by Union Carbide Corporation.
[2]Supplied by Henkel, Inc.
[3]Supplied by Sherex Chemical Company.

EXAMPLE III

The following composition of the present invention is prepared in a manner similar to that described in Example I.

| | |
|---|---|
| Dodecane[1] | 10.00% |
| Jaguar HP-60 | 1.75 |
| Ditallow methyl amine hydrochloride[2] | 0.25 |
| Polyox WSR-205[3] | 0.10 |
| Methyl paraben[4] | 0.20 |
| Propyl paraben[4] | 0.10 |
| Perfume | 0.80 |
| Distilled Water q.s. | 100.00% |

[1]Supplied by Humphrey Chemical Company.
[2]Supplied by Sherex Chemical Company.
[3]Supplied by Union Carbide Corporation.
[4]Supplied by Inolex Corporation.

EXAMPLE IV

The following composition is prepared in a manner similar to that described in Example I except that the silicone and the Lutonal are preblended.

| | |
|---|---|
| Dow Corning Fluid 345[1] (cyclic silicone having 5 dimethyl siloxane groups) | 7.00% |
| Lutonal 1C 115[2] (polyvinyl isobutyl ether) | 0.02 |
| Corn starch powder[3] | 3.50 |
| Stearyl benzyl dimethyl ammonium chloride[4] | 0.30 |
| Ethanol | 7.00 |
| Distilled Water q.s. | 100.00% |

[1]Supplied by Dow Corning Corporation.
[2]Supplied by BASF.
[3]Supplied by CPC International, Inc.
[4]Supplied by Hexcel-Fine Organics.

EXAMPLE V

The following composition was prepared:

| | |
|---|---|
| Union Carbide 7158 Silicone Fluid | 8.000% |
| Lutonal 1C 115 | 0.008 |
| Jaguar HP-60 | 1.100 |
| Ethanol | 8.000 |
| Adogen 442[1] (90% active) | 0.240 |
| Perfume | 0.500 |
| Distilled Water q.s. | 100.000% |

[1]Ditallow dimethyl ammonium chloride supplied by Sherex Chemical Company.

The above composition was prepared by placing 76.08 grams of the volatile silicone, 400 grams of distilled water and 4 grams of a stock solution consisting of 2% Lutonal 1C 115 in volatile silicone into a mix tank. The stock solution had been prepared earlier by dissolving 2 grams of the ether in 98 grams of the volatile silicone and mixing with a magnetic stirrer for 24 hours. A pre-mix was prepared by dispersing 2.4 grams of the quaternary and 11 grams of Jaguar HP-60 in 80 grams of ethanol. This was mixed with a magnetic stirrer for 10 minutes at ambient temperature. This pre-mix was then added to the main mix tank and sheared with a Ultra Turrax Model 45S4 for five minutes. To the batch were then added 421 grams of distilled water and 5 grams of perfume. A Lightnin ® mixer was used to complete mixing the batch for 15 minutes.

What is claimed is:

1. A hair conditioning composition in the form of an emulsion comprising:

a. From about 1% to about 13% of a volatile hair conditioning agent having a boiling point in the range of from about 99° C. to about 260° C. and a solubility in water of less than about 0.1% selected from the group consisting of hydrocarbons, silicones and mixtures thereof;

b. From about 0.1% to about 8% of a substantially nonionic, water-soluble polymer having a viscosity in excess of about 200 poises at a shear of about $10^{-2}$ sec$^{-1}$ while having a viscosity less than about 9 poises at a shear of about 500 sec$^{-1}$;

c. From about 0.05% to about 4% of a quaternary ammonium salt having at least one hydrocarbon chain having from about 12 to about 22 carbon atoms;

d. From about 0.05% to about 4% of a salt of a fatty amine; and e. Water.

* * * * *